United States Patent [19]

Konishi

[11] Patent Number: 4,889,720

[45] Date of Patent: Dec. 26, 1989

[54] SUSTAINED RELEASE DOSAGE FORM FOR USE WITH TISSUES OF THE ORAL CAVITY

[75] Inventor: Ryoji Konishi, Kagawa, Japan

[73] Assignee: Teikoku Seiyaku Kabushiki Kaisha, Kagawa, Japan

[21] Appl. No.: 90,916

[22] Filed: Aug. 31, 1987

[30] Foreign Application Priority Data

Sep. 1, 1986 [JP] Japan ................................ 206590

[51] Int. Cl.$^4$ ............................................. A61F 7/02
[52] U.S. Cl. .................................... 424/448; 424/435
[58] Field of Search ............... 424/435, 447, 448, 449; 604/304, 307, 897

[56] References Cited

U.S. PATENT DOCUMENTS

| | | | |
|---|---|---|---|
| 688,446 | 12/1901 | Stempel | 604/304 |
| 3,536,809 | 10/1970 | Applezweig | 424/447 |
| 3,598,122 | 8/1971 | Zaffaroni | 424/449 |
| 3,731,683 | 5/1973 | Zaffaroni | 424/448 X |
| 3,996,934 | 12/1976 | Zaffaroni | 424/448 X |
| 4,226,848 | 10/1980 | Nagai et al. | 424/447 |
| 4,704,119 | 11/1987 | Shaw et al. | 604/304 |

*Primary Examiner*—Nancy A. B. Swisher
*Attorney, Agent, or Firm*—Burns, Doane, Swecker & Mathis

[57] ABSTRACT

A drug reservoir containing an active substance such as a drug is formed on an adhesive layer which can adhere to an oral mucosal membrane. A polymer, which does not dissolve with saliva, is further coated on the drug reservoir as a drug release controlling layer to form an entire oral cavity sustained release dosage form. A drug impermeable layer can be formed between the adhesive layer and the drug reservoir.

10 Claims, 1 Drawing Sheet

SUSTAINED RELEASE DOSAGE FORM FOR USE WITH TISSUES OF THE ORAL CAVITY

BACKGROUND OF THE INVENTION

The present invention is concerned with a multi-layer sustained release dosage form for use in the oral cavity. More specifically, in the invention includes a portion or layer which contains an active substance, this portion or layer hereafter referred to as a drug reservoir, and a drug release controlling layer which is formed with a nonsaliva dissolving polymer. The drug reservoir and the drug release controlling layer are formed over an adhesive layer, the latter adhering to oral cavity tissue. If desirable, a drug impermeable layer is formed between the drug reservoir and the adhesive layer. The dosage form of the present invention sticks to the oral tissue, and releases the drug continuously over a long period at a constant rate, with saliva permeating through the drug release controlling layer. The drug action is sustained with the drug being absorbed from the oral cavity via, for example, an oral cavity tissue such as a mucosal membrane.

Although oral administration and injection are currently the main administration routes for drug therapy, a safer and more effective administration route and device is desirable for various reasons. The oral cavity tissue including the mucosal membrane is one of the few possible administration sites, and there have been numerous reports on this possibility. One example is sublingual tablets. Such tablets can be used for a drug whose quick action is desirable, such as nitroglycerin, but the tablets cannot be retained under the tongue for a long period of time. Drug action in the oral cavity can be relatively prolonged using buccal tablets, and sustained action can be achieved by changing the disintegration time of the tablets. However, the disintegration time varies with the administration method and also from one subject to another. Although buccal tablets have been reported, see, for example, Tokkaisho 58-213709, even with these dosage forms drugs can be released into the oral cavity quantitatively for a long period of time for a prolonged constant drug absorption.

DISCLOSURE OF THE INVENTION

It is accordingly an object of the invention to provide a controlled release dosage form which can be retained in the oral cavity for a prolonged period.

It is another object of the invention to provide a controlled release dosage form, as above, which provides controlled release of an active substance at a constant rate.

It is yet another object of the invention to provide a controlled release dosage form, as above, which is usable with active substances having short half lives.

It is still another object of the invention to provide a controlled release dosage form, as above which does not give a "foreign body" sensation in the oral cavity.

It is yet another object of the invention to provide a controlled release dosage form, as above, which presents less of a possibility of mis-swallowing.

These objects and other area achieved by a controlled release dosage form for application to a tissue in the oral cavity mucous membrane, comprising a reservoir containing an active substance, a controlled release layer positioned adjacent the reservoir and surrounding at least a first portion of the reservoir, the controlled release layer delaying the release of the active substance, and adhesive means for adhering the dosage form to the oral cavity tissue.

The objects of the invention are also achieved by a method for preparing the dosage form of the invention and by a method for administering the dosage form.

BRIEF DESCRIPTION OF THE DRAWINGS

For a complete understanding of the invention, reference should by made to the following detailed description and the drawings, wherein.

DETAILED DESCRIPTION OF THE PREFERRED EMBODIMENTS

Figure 1:
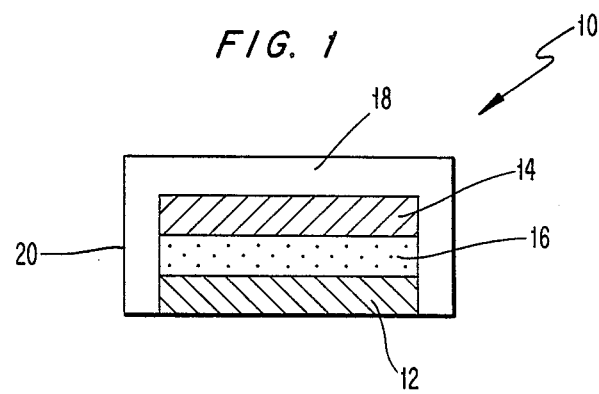
FIG. 1 is a cross-sectional view of one embodiment of the dosage form of the invention.

The inventors have found that the problems associated with conventional dosage forms used, for example, in the oral cavity can be solved, and have reached the present invention by forming a reservoir containing an active substance such as a drug, and a drug release controlling layer, i.e., a controlled release layer, which is composed of a non-saliva dissolving polymer. It is to be understood that reference hereinafter to "drug" or "drugs" broadly encompasses "active substances", i.e., substances which have a physiological effect.

The drug reservoir and drug release controlling layer are positioned over an adhesive layer which sticks to tissue in the oral cavity such as an oral mucosal membrane. Also, if desirable, a drug impermeable layer can be positioned between the adhesive layer and the drug reservoir (see FIG. 1). That is, the present invention offers a sustained release dosage form for use in conjunction with oral cavity tissue which includes a drug reservoir and a drug controlling layer, which is made from a non-saliva dissolving polymer, over an adhesive layer, which sticks to the oral cavity mucosal membrane, and also, if desirable, a drug impermeable layer is formed between the adhesive layer and the drug reservoir.

The following are examples of the polymers which can be used in the controlling release layer; ethyl methacrylate-ethyl trimethylammonium chloride methacrylate copolymer (Eudragit RS), dimethylaminoethyl methacrylate-methyl methacrylate copolymer (Eudragit E), 2-methyl-5-vinylpyridine-2-methylacrylic acid-methacrylic acid copolymer, and other acrylic copolymers, carboxymethylethyl cellulose, cellulose acetate phthalate, and other cellulose derivatives, polyvinylacetal diethylaminoacetate, polyvinyl alcohol, vinylacetate resin, cellac, gelatin, etc.

A wide range of synthetic polymers and natural polymers can be used. The following compounds can be added to the above polymers to form a film which has good elasticity and release pattern: polyethylene glycol, propylene glycol, and other glycols, glycerin, 1,3-butane diol, and other polyalcohols, glycerin fatty acid ester, triacetin, citric acid esters etc. as a plasticizer. Although in most cases the drug release controlling layer does not contain any active substances, small amounts of one or more drugs can be incorporated in this layer for quick drug release after application.

For a drug reservoir layer, tablets which are made from excipients and drugs using conventional methods, or any type of drug container which adsorbs the drug, can be used. The following are examples of excipients: lactose, fructose mannitol, monobasic calcium phosphate, aluminum silicate, magnesium silicate, crystalline cellulose, starch, dextrin, polyvinylpyrrolidone, polyacrylic acid resin, hyroxypropyl cellulose, hydroxypropyl methylcellulose, etc., or mixture of more than two or more of these compounds. As a drug container, polymer film or a fibrous material which easily adsorbs drugs can be used.

Drugs administerable in the present invention include those used for the treatment of oral cavity disease or for systemic use, for example, benzodiazepines, psychotherapeutic drugs, anti-ulcer drugs, spasmolytics, antihistamines, cardiotonics, antiarrhymic drugs, diuretics, antihypertensives, vasocontrictors, vasodilators, nitrous acid drugs, calcium antagonists, hormones, vitamins, anti-smoking drugs, anti-cancer drugs, antibiotics, chemotherapeutic agents, etc. Drugs whose concentration in blood has to be maintained for a long period of time for the pharmacological effect, or drugs which are more effective when they act on the digestive tract directly for a long period of time, are preferably incorporated in the present invention.

As a drug impermeable layer, there may be used ethylcellulose, cellulose acetate, and other cellulose derivatives, dimethylaminoethyl methacrylatemethyl methacrylate copolymer (Eudragit E), and other acrylic copolymers, or other synthetic polymers.

For the adhesive layer one or more than one water soluble polymers are used, together with a plasticizer and a water insoluble compound or a sparingly water soluble compound, and the mixture thus formed is usually formed into a film. This layer shows adhesiveness upon gradual dissolution or gelation with saliva.

With reference to FIG. 1, one embodiment of the sustained release dosage form of the present invention is indicated generally by the number 10. This embodiment, useful particularly in the oral cavity, has a multilayer structure. That is, on an adhesive layer 12 a drug reservoir layer 14 is formed and, if desirable, a drug impermeable layer 16 is formed between the adhesive layer 12 and the drug reservoir layer 14, and then a drug release controlling layer 18 is formed to cover the whole system. As shown in FIG. 1, the drug release controlling layer 18 preferably extends along the edges of the reservoir, adhesive and drug impermeable layers to form a side coating 20.

With regard to thickness, generally, thinner is preferable. That is, the thickness of the dosage form can be within the range generally used in the tabletting art, or may be thinner than that generally used, in order to reduce the "foreign body" sensation encountered when utilizing tablets sublingually. The dosage form, in a preferred embodiment, has a thickness which characterizes it as a "patch".

With regard to the shape, the dosage form can be any shape such as circular, oval, square or rectangular depending on the site of application. For example, when applied to the gingival tissue, there can be used an oval shape with a shorter diameter of about 3-10 mm and a longer diameter of about 5-30 mm, more preferably about 5-8 mm in shorter diameter and about 5-20 mm in longer diameter. When applied to other cavity tissue such as mucosal membranes, a circle of about 3-20 mm diameter is preferable with about 5-10 mm diameter circle being more preferable.

To prepare the dosage form of the present invention, components for each layer described are dissolved in appropriate solvents and formed into the desired shape. For example, each component in solvent is spread, the solvent evaporated, and a film of each layer is obtained. Each of these layers is piled in order, glued and dried, and the resulting multilayered structure is then cut into a desirable size and shape. For solvents to prepare the layers, any solvent can be used as long as it dissolves and is nonactive to the components. Water, methanol, ethanol and acetone are preferable and mixtures of two or more solvents also can be used.

The sustained release dosage form of the invention has the following advantages over previously known dosage forms, particularly when used in the oral cavity. Since the dosage form of the invention releases drugs at a constant rate for a long period of time, the frequency of drug administration can be reduced. Since the drug concentration is maintained for a long period of time, the dose can be reduced, leading to less side effects and more efficacy by sustained administration. Drugs which have short half lives or are susceptible to liver metabolism can be formulated. Bioavailability is high. The dosage form of the invention eliminates pain associated with subcutaneous or intra-muscular injection.

Since it can be a patch dosage form, the dosage form can be retained in the oral cavity for a long period of time while giving less "foreign body" sensation compared to sublingual tablets or buccal tablets. Also, the dosage form of the invention has less possibility of misswallowing and it can be used safely for infants and during sleeping. Since one of the purposes of the present invention is to provide absorption from the digestive tract and direct action on the digestive tract, the invention has a wide range of application. By changing the composition, thickness, size etc. of the drug reservoir layer and drug release controlling layer, appropriate drug release rate and duration of release can be obtained depending on the desired drug effect.

The following are examples of the formulas and experiments which provide a further detailed explanation of the invention.

EXAMPLE 1

A. Preparation of Drug Release Controlling Layer

| Component | Amount |
|---|---|
| Eudragit RS-100 | 8.0 g |
| Polyethylene Glycol 400 | 0.8 g |
| Ethanol | 12.0 ml |

8.0 g of Eudragit RS-100 is dissolved in 12.0 ml of ethanol. Polyethylene glycol 400 (0.8 g) is added to the solution, stirred to obtain a uniform solution, and then degassed.

B. Preparation of Drug Reservoir Layer

| Component | Amount |
|---|---|
| Eudragit RL-PM | 7.5 g |
| Polyethylene Glycol 1500 | 3.0 g |
| Prostaglandin $E_2$ | 0.026 g |
| Ethanol | 12.0 ml |

Eudragit RL-PM (7.5 g) is dissolved in 12 ml of ethanol and polyethylene glycol 1500 (3.0 g) is added to this solution. Then Prostaglandin E$_2$ is added, stirred until the solution becomes uniform, and degassed.

C. Preparation of Drug Impermeable Layer

| Component | Amount |
|---|---|
| Ethylcellulose | 15.0 g |
| Castor Oil | 8.0 g |
| Ethanol | 100.0 ml |

Ethylcellulose (15.0 g) and castor oil (8.0 g) are dissolved in 100 ml of ethanol, stirred until the solution becomes uniform, and degassed.

D. Preparation of Adhesive Layer

| Component | Amount |
|---|---|
| Ethylcellulose | 1.0 g |
| Polyacrylic Acid | 5.0 g |
| TiO$_2$ | 0.4 g |
| Glycerin Fatty Acid Ester | 1.0 g |
| Ethanol | 60.0 ml |

Ethylcellulose (1.0 g), polyacrylic acid (5.0 g), TiO$_2$ (0.4 g), and glycerin fatty acid ester (1.0 g) are dissolved in 60 ml of ethanol, stirred until the solution becomes uniform, and then degassed.

E. Preparation of Sustained Release Dosage Form

The drug release controlling layer, drug reservoir layer, drug impermeable layer, and adhesive layer are spread separately and dried at 35° C. After partial drying (approximately 50%) these layers are piled in order, well attached, and further dried. After drying is complete, the piled and attached layers are cut into a desirable size and the sides are coated to obtain a four-layer film with 0.8 mm in thickness.

EXAMPLE 2

A four-layer film dosage form is obtained using the components described below and with the same method as that in Example 1.

Drug Release Controlling Layer:

| Componenet | Amount |
|---|---|
| Eudragit RS-100 | 8.0 g |
| Polyethylene Glycol 400 | 0.8 g |
| Acetone | 12.0 ml |

Drug Reservoir Layer:

| Component | Amount |
|---|---|
| Cellulose acetate | 4.0 g |
| Triacetin | 2.0 g |
| Mitomycin C | 0.15 g |
| Acetone | 17.0 ml |

Drug Impermeable Layer:

| Component | Amount |
|---|---|
| Cellulose acetate-phthalate | 8.0 g |
| Triacetin | 3.0 g |
| Acetone | 17.0 ml |

Adhesive Layer:

| Component | Amount |
|---|---|
| Eudragit RL-100 | 0.2 g |
| Polyacrylic acid | 12.0 g |
| Polyethylene glycol 400 | 2.0 g |
| Ethanol | 85.8 ml |

EXAMPLE 3

A four-layer film dosage form is obtained using the components described below and with the same method as that in Example 1.

Drug Release Controlling Layer:

| Component | Amount |
|---|---|
| Cellulose acetate-phthalate | 5.0 g |
| Diethyl phthalate | 2.0 g |
| Ethanol | 10.0 ml |

Drug Reservoir Layer:

| Component | Amount |
|---|---|
| Crystalline cellulose | 5.0 g |
| Magnesium stearate | 0.1 g |
| Bupranolol hydrochloride | 0.5 g |

Drug Impermeable Layer:

| Component | Amount |
|---|---|
| Vinylacetate resin | 10.0 g |
| Methanol | 10.0 ml |

Adhesive Layer:

| Component | Amount |
|---|---|
| Vinylacetate resin | 5.0 g |
| Polyacrylic acid | 5.0 g |
| Polyethylene glycol 400 | 4.0 g |
| Ethanol | 36.0 ml |

EXAMPLE 4

A three-layer film dosage form is obtained using the components described below and with the same method as that in Example 1.

Drug Release Control Layer:

| Component | Amount |
|---|---|
| Polyvinyl alcohol | 5.0 g |
| 1,3-Butanediol | 1.5 g |
| Water | 15.0 ml |

Drug Reservoir Layer:

| Component | Amount |
|---|---|
| Polyvinyl alcohol | 5.0 g |
| Polyethylene glycol | 7.0 g |
| Decalinium hydrochloride | 0.089 g |
| Water | 20 ml |

Adhesive Layer:

| Component | Amount |
| --- | --- |
| Ethylcellulose | 0.2 g |
| Polyacrylic acid | 5.0 g |
| Castor oil | 0.5 g |
| Ethanol | 60.0 ml |

EXAMPLE 5

A four-layer film dosage form is obtained using the components described below and with the same method as that in Example 1.

Drug Release Control Layer:

| Component | Amount |
| --- | --- |
| Vinylacetate resin | 10.0 g |
| Polyethylene glycol 400 | 2.0 g |
| Methanol | 15.0 ml |

Drug Reservoir Layer:

| Component | Amount |
| --- | --- |
| Hydroxypropyl cellulose | 5.0 g |
| Polyethylene glycol 400 | 0.5 g |
| Isosorbide dinitrate | 1.84 g |
| Ethanol | 20.0 ml |

Drug Impermeable Layer:

| Component | Amount |
| --- | --- |
| Ethylcellulose | 7.5 g |
| Castor oil | 1.5 g |
| Ethanol | 41.0 ml |

Adhesive Layer:

| Component | Amount |
| --- | --- |
| Vinylacetate resin | 5.0 g |
| Polyvinylpyrrolidone | 2.0 g |
| Ethanol | 15.0 ml |

EXAMPLE 6 AND COMPARATIVE EXAMPLE 1

Figure 2:
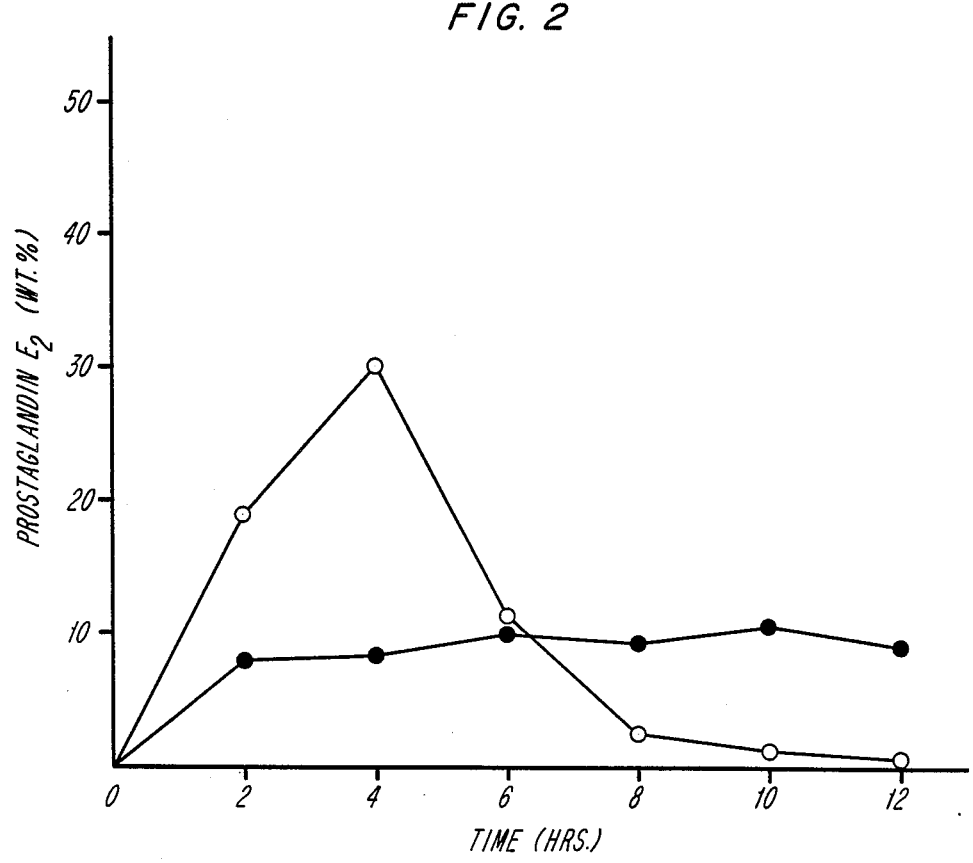
FIG. 2 is a plot of percent dissolution vs. time for the dosage form of Example 6 and for a comparative example.

In vitro drug dissolution rate and duration of drug release were measured for the four-layer film dosage form in Example 1 and the same formulation without the drug release control layer was measured as a comparison sample. Dissolution tests were performed according to the rotating basket method (JP Pharmacopeia 10) with 100 ml of dissolution fluid at 25 r.p.m. at 37° C. The results are shown in FIG. 2. This figure shows the percentage of the drug (Prostaglandin $E_2$) released compared to the total amount of drug in the dosage form for each 2 hour interval.

EXAMPLE 7

To examine the correlation between the in vitro dissolution and the in vivo release, the amount of drug remaining in the dosage form was measured. The four-layer film in Example 1 was tested in a human subject for 6 hours and the amount of drug remaining was measured. More than 70% of the drug was found to be remaining.

EXAMPLE 8

The four-layer film in Example 1 was tested in rats and the effectiveness of multiple dosing on indomethacin-induced ulcer was examined. There was a significant difference between prostaglandin single dosing and multiple dosing.

Although the invention has been described in terms of specified embodiments which are set forth in detail, it should be understood that this is by way of illustration only and that the invention is not necessarily limited thereto, since alternative embodiments and operations techniques will become apparent to those skilled in the art in view of the disclosure. Accordingly, modifications are contemplated which can be made without departing from the spirit of the described invention.

What is claimed is:

1. A controlled release dosage form for application to oral cavity tissue, comprising:
   an adhesive layer having a first side adherable to oral cavity tissue;
   a reservoir containing an active substance positioned over a second side of the adhesive layer; and
   a controlled release layer covering the reservoir and providing for a delayed release of the active substance into the oral cavity wherein the first side of the adhesive layer adherable to oral cavity tissue is left uncovered by the controlled release layer.

2. A controlled release dosage form as claimed in claim 1, wherein said reservoir comprises a layer, and wherein said adhesive layer is positioned along one side of said reservoir layer, and said controlled release layer is positioned along both a side of said reservoir layer opposite said one side and along an edge of said reservoir layer.

3. A controlled release dosage form as claimed in claim 1, wherein said dosage form includes an impermeable layer positioned between said reservoir and said adhesive layer.

4. A controlled release dosage form as claimed in claim 1, wherein said dosage form is oval-shaped.

5. A controlled release dosage form as claimed in claim 4, wherein said oval-shaped dosage form has a shorter diameter of from about 3 to about 10 mm and a longer diameter of from about 5 to about 30 mm.

6. A controlled release dosage form as claimed in claim 1, wherein said controlled release layer comprises ethyl methacrylate-ethyl trimethylammonium chloride methacrylate copolymer, dimethylaminoethyl methacrylate - methylmethacrylate copolymer, 2-methyl-5-vinylpyridine-2-methacrylic acid - methacrylic acid copolymer, carboxymethylethyl cellulose, cellulose acetate - phthalate, polyvinylacetal diethylamino acetate, polyvinyl alcohol, vinyl acetate resin, cellac or gelatin.

7. A controlled release dosage form as claimed in claim 6, wherein said controlled release layer includes polyethylene glycol, propylene glycol, glycerin, 1,3-butane diol, glycerin-fatty acid ester, triacetin, or a citric acid ester.

8. A controlled release dosage form as claimed in claim 3 wherein said impermeable layer comprising ethylcellulose, cellulose acetate, or dimethylaminoethyl methacrylate - methylmethacrylate copolymer.

9. A controlled release dosage form as claimed in claim 1, wherein said adhesive layer includes at least one water-soluble polymer, a plasticizer and a water-insoluble or sparingly water-soluble compound, and wherein said adhesive layer exhibits adhesiveness to tissue of the oral cavity upon gradual dissolution or gelation of said adhesive layer with saliva.

10. A controlled release dosage form as claimed in claim 1, wherein said active substance comprises a benzodiazepine, a psychotherapeutic drug, an anti-ulcer drug, a spasmolytic, an antihistamine, a cardiotonic, an antiarrhymic drug, a diuretic, an antihypertensive, a vasoconstrictor, a vasodilator, a nitrous acid drug, a calcium antagonist, a hormone, a vitamin, an anti-smoking drug, an anti-cancer drug, an antibiotic, or a chemotherapeutic agent.

* * * * *